United States Patent
Cama

[11] Patent Number: 5,839,430
[45] Date of Patent: Nov. 24, 1998

[54] COMBINATION INHALER AND PEAK FLOW RATE METER

[76] Inventor: Joseph Cama, 213 Pine St., Towanda, Pa. 18848

[21] Appl. No.: 785,164

[22] Filed: Jan. 13, 1997

Related U.S. Application Data

[60] Provisional application No. 60/016,172, Apr. 26, 1996.
[51] Int. Cl.⁶ .......................... A61M 11/00; A61M 15/00; A61M 16/10
[52] U.S. Cl. ............................ 128/200.14; 128/203.12; 128/204.23; 600/538; 600/540
[58] Field of Search ...................... 128/200.14, 200.23, 128/200.24, 203.12, 200.16, 203.15, 203.21, 204.23, 725, 727; 600/538, 540

[56] References Cited

U.S. PATENT DOCUMENTS

| | | |
|---|---|---|
| 4,944,306 | 7/1990 | Alvino . |
| 4,984,158 | 1/1991 | Hillsman ........................ 128/200.14 X |
| 5,040,527 | 8/1991 | Larson et al. . |
| 5,137,026 | 8/1992 | Waterson et al. ........................ 128/725 |
| 5,224,487 | 7/1993 | Bellofatto et al. . |
| 5,363,842 | 11/1994 | Mishelevich et al. ............. 128/200.14 |
| 5,394,866 | 3/1995 | Ritson et al. ....................... 128/200.14 |
| 5,404,871 | 4/1995 | Goodman et al. ................. 128/200.14 |
| 5,431,154 | 7/1995 | Seigel et al. ....................... 128/200.14 |
| 5,518,002 | 5/1996 | Wolf et al. ............................... 128/725 |
| 5,522,380 | 6/1996 | Dwork ................................ 128/200.23 |
| 5,540,234 | 7/1996 | Lalui .................................. 129/727 X |
| 5,565,630 | 10/1996 | Shene .................................. 128/727 X |

FOREIGN PATENT DOCUMENTS

| | | | |
|---|---|---|---|
| 1 230 505 | 12/1987 | Canada ............................. 128/200.23 |
| 0 769 303 | 4/1997 | European Pat. Off. .......... 128/200.23 |

OTHER PUBLICATIONS

Aerosol Delivery Systems, AARC Times, May 1995, vol. 19(5) p. 43.
Peak Flow Rate Meters, AARC Times, Jul. 1995, p. 33.
Micro Spirometer, Product brochure, Micro Medical Ltd., England
MicroPlus Spirometer, Product brochure, Micro Medical Ltd., England.

Primary Examiner—Mary Beth Jones
Assistant Examiner—Dinh X. Nguyen
Attorney, Agent, or Firm—Sherman Pernia

[57] ABSTRACT

The utility and elements of a metered dose inhaler, a spacer device and a peak respiratory flow rate meter are combined in a single personally portable device. The present device provides a tool for improving compliance of patients with asthma and other pulmonary disorders with their prescribed treatment regimens. This is accomplished in by combining therapeutic and diagnostic devices in a single personal device.

12 Claims, 7 Drawing Sheets

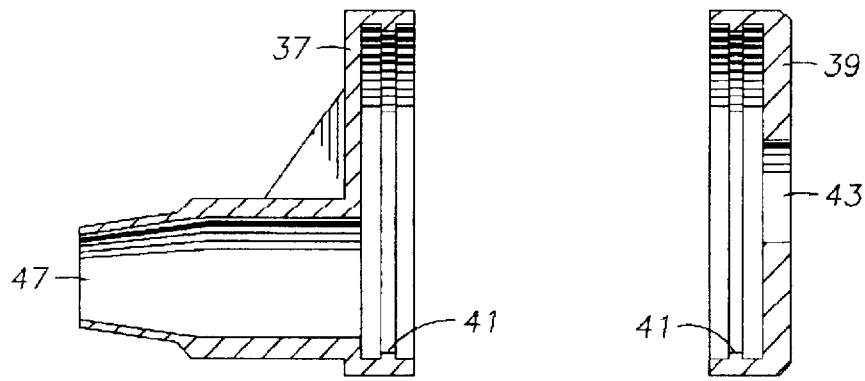
FIG. 5  FIG. 6
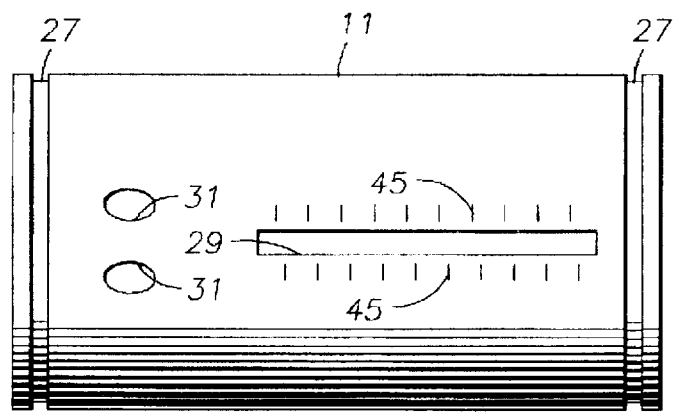
FIG. 7
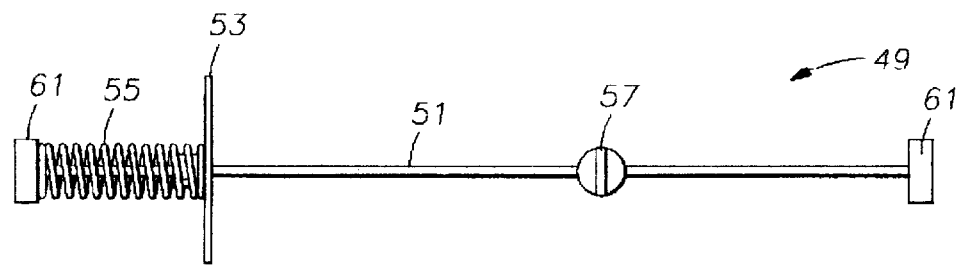
FIG. 8

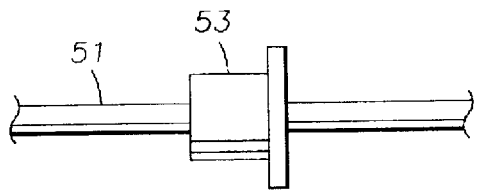
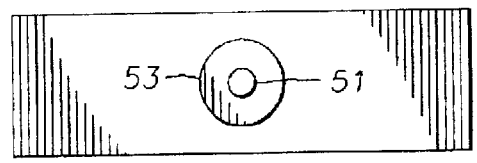
FIG. 9a     FIG. 9b
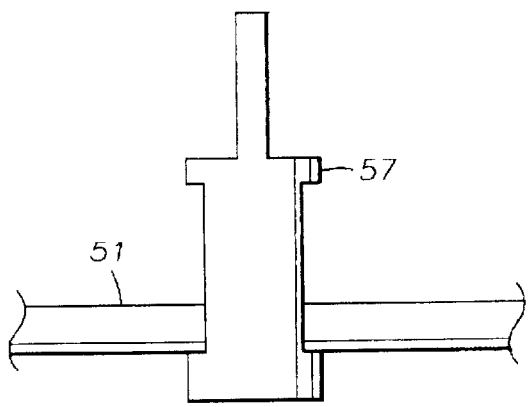
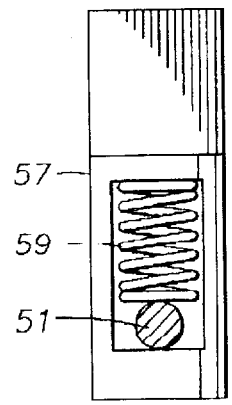
FIG. 10a     FIG. 10b
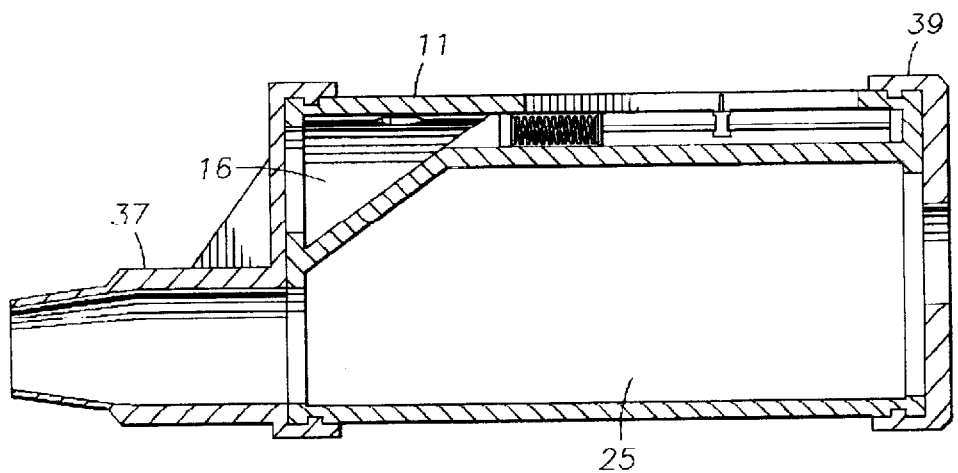
FIG. 11

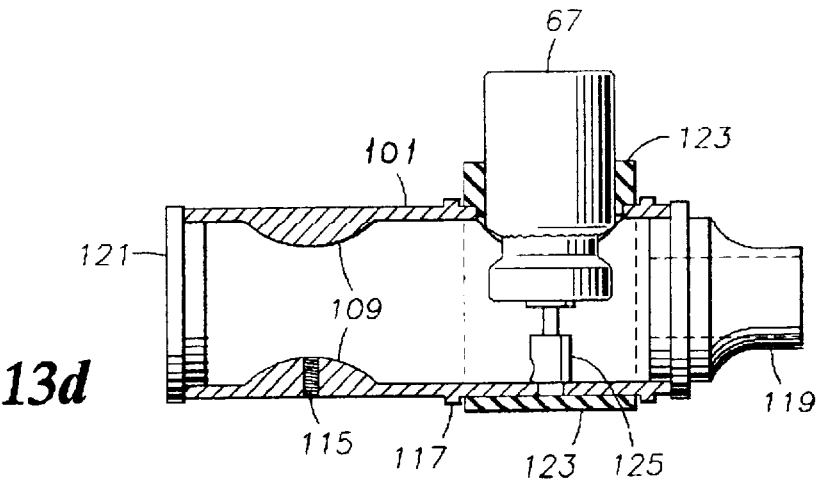
FIG. 13d
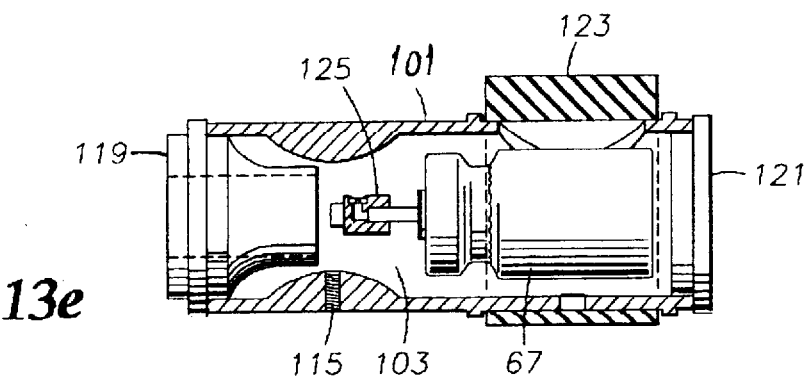
FIG. 13e
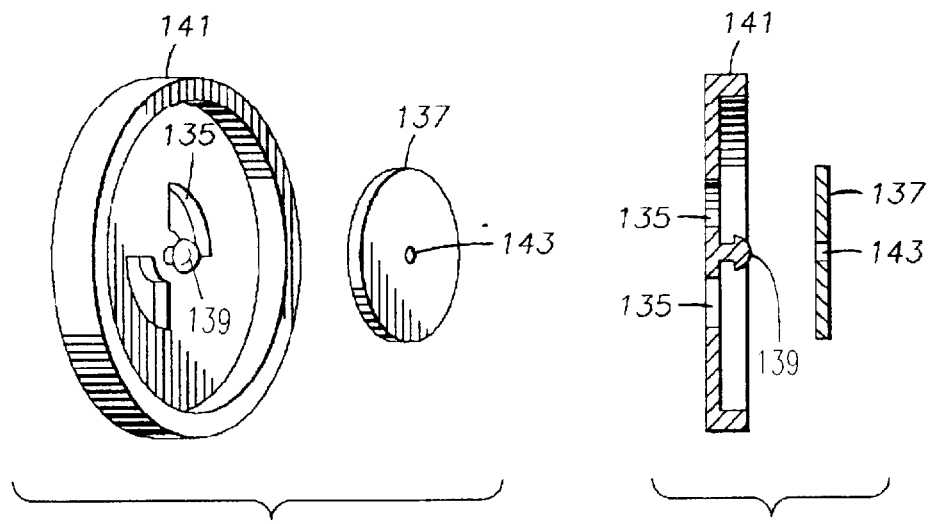
FIG. 14a   FIG. 14b

COMBINATION INHALER AND PEAK FLOW RATE METER

The present application claims the benefit of prior filed Provisional application Ser. No. 60/016,172, filed 26 Apr. 1996 to which the present application is a regular U.S. national application.

FIELD OF THE INVENTION

The present invention is in the field of respiratory therapy. More specifically, the present invention is in the field of respiratory therapy and personal respiratory care devices.

BACKGROUND OF THE INVENTION

Inhalers

Inhalers are personal medication devices, generally pocket or purse size, and used for the administration of a variety of therapeutic aerosols. Such devices include metered dose inhalers (MDI), dry powder inhalers, small and large volume nebulizers, and ultrasonic nebulizers.

Over the past 20 years, the MDI has emerged as the preferred device for delivering aerosolized medications to patients with asthma. Therapeutic MDI use is now well established, and a large portion of Americans with chronic lung disorders not only use MDI products for relief of symptoms, but use them prophylactically to avoid acute episodic attacks. However, the component technologies of the MDI (the canister, propellants, and metering device) have changed little over this time.

Generally, MDIs are nebulizers, in which a drug and a dispersal agent are suspended in a propellant gas, such as FREON. This formulation is contained in a small pressurized canister and released by actuation of a metering device. MDIs comprise the following components:

(1) a canister containing a pharmaceutical formulation and a metering valve that controls the amount of drug dispersed during a single actuation.

(2) a holder for housing and actuating the canister and adapting the aerosol cloud for inhalation by the user.

(3) a nozzle fitting for receiving and directing the aerosol expelled from the canister on activation.

Actuation of the canister results in a cloud or plume of aerosol particles. The volume of gas per dose ranges roughly from 15 to 20 mL per puff depending on the device. The weight of the canister is proportional to the number of doses remaining in the canister, which allows one to determine the number of doses dispensed to within 25%.[12] MDI canisters produce particles of various sizes. Some of these particles are as large as $40\mu$, but generally, only $1\mu$ to $5\mu$ particles are in the therapeutic range.

Improper handling and use technique has been demonstrated to detrimentally impact efficacy of inhaler based therapy. 50% of patients are reported to misuse their inhalers, with the most frequent technique problems being:

(1) improper coordination of activation and inspiration, (2) too rapid an inspiration rate (3) failure to hold breath (4) failure to titrate dosage (5) failing to shake the canister.

Although many factors influence the efficacy of an inhaler based therapeutic regimen, one of the most important factors is patient compliance with a titration schedule. A major finding of the consensus conference on guidelines for respiratory aerosol therapy (American Association of Respiratory Care, Aerosol Therapy Committee) is that aerosol delivered drugs used in respiratory therapy need be titrated to achieve maximum therapeutic effect. As used here, titration is the on-going monitoring of a patient's respiratory condition to determine an acute minimum effective therapeutic dose (amount and frequency) for maintaining the patient's respiratory condition above a particular level of performance (peak expiratory flow rate). This can be most effectively accomplished only by the patient him/herself.

Spacers (Aerosol Chambers)

Spacers are hollow or chambered devices into which a dose of an inhaler's content may be dispensed before or during an act of inhalation by the user. Spacers/aerosol chambers vary in shape from cylindrical to plume or cone shaped and including collapsible chambers. In some cases, the aerosol chamber width and length are optimized to capture the larger aerosol particles while increasing the number of particles delivered in the therapeutic range. For some applications, the lumen of the aerosol chamber is coated with an anti-static agent to increase the availability of respirable particles.

Spacers may include a one-way valve to assist the patient with coordinating the act of inspiration with actuation. A spacer/one-way valve combination can provide a holding chamber for the aerosolized drug until the patient inhales, and ensure that the drug is delivered only during inspiration. This alleviates the problems associated with patient coordination by separating the act of inspiration from the act of actuation of the canister. Another feature a spacer may include is a flow-modulating mechanism that promotes a proper inspiration rate.

A primary purpose of the spacer is to retain a portion of the dispensed formulation that would otherwise "rain-out" in the patient's mouth and throat (and then be swallowed), by having it rain-out in the spacer instead. This is a very important feature as it reduces the side effects associated with oropharyngeal deposition of the aerosol medicant and its subsequent ingestion. A spacer can also reduce the "Cold FREON Effect", which causes some patients to stop inhaling when the cold blast of FREON propellant hits the back of the user's throat.

Spacers are known in the art. Generally, most spacers are independent devices which are used in association with an inhaler. In these cases, a separate inhaler device is attachable to the spacer through the mouthpiece of the inhaler housing. For examples, see U.S. Pat. Nos. 4,470,412 and 5,012,803 or the AeroChamber® with FLOWSIGNAL™ (Monaghan Medical Corp., N.Y.). In at least one other case, an MDI canister may be directly attachable to a spacer (see U.S. Pat. No. 5,040,527).

Peak Expiratory Flow Rate Meters (PEFR)s

A PEFR is a device for measuring the maximum rate at which air is expelled out of the lungs during the course of an exhalation. PEFRs typically comprise a housing with a calibrated scale, a mouth-piece port, an indicator, and an expiratory port. These devices have different types of pressure sensors, including Thorpe tube type sensors, rotameter type sensors and spirometers. Other pressure sensors use a spring loaded piston that slides on a rod, or a flexible vane affixed at one end. Examples of applications using such sensors include U.S. Pat. No. 4,944,306 to Alvino and U.S. Pat. No. 5,224,487 to Bellofatto et al., which are incorporated herein by reference.

Personal PEFR devices are known in the art as separated units. Personal PEFR devices are not currently known in combination with inhalers and/or spacers.

Many pulmonary disorders affect the size and compliance of the pulmonary airways and alter a person's ability to rapidly move air out of the lungs. Therefore, a measurement of a person's ability to rapidly move air out of the lungs is diagnostic for such disorders. In use, a person is directed to explosively exhale—with a maximal expiratory effort—into the PEFR and a peak expiratory flow rate for the person is determined from the device. A subnormal determination or a determination that falls below a baseline level is diagnostic of respiratory compromise.

The incidence, mortality, and cost of caring for patients with asthma has been increasing over the past few decades. Guidelines for the diagnosis and management of asthma patients published by National Asthma Education and Prevention Program (NAEPP) have emphasized that monitoring peak expiratory flow rate is a sensitive and useful indicator for detecting compromise of pulmonary function and predicting the need for personal or professional intervention. This is because a patient's normal peak expiratory flow rate may be reduced to 75% or less by the time auscultation can detect wheezing. This is known as asymptomatic deterioration of pulmonary function. Therefore, a method of monitoring the on-set and course of airway obstruction, assessing an asthmatic's response to medication, and predicting impending respiratory distress would help reduce asthma mortality and asthma-related medical care costs.

Because clinical signs and patients' symptoms of asthma are so poorly correlated to lung dysfunction, use of a personal PEFR is an important tool in asthma management. Patients who fail to appreciate the true changes in their lung function frequently delay consultation with their physician. This period of delay has been implicated as a contributing factor in the increased severity of and mortality from asthma. Studies have also shown that patients who properly use a PEFR, use their medications less frequently and more appropriately, and therefore, reduce the side-effects caused by excess exposure to medicants.

Use of a personal PEFR for monitoring peak expiratory flow rate would be beneficial for: early detection of pulmonary deterioration and intervention before dysfunction worsens; monitoring the treatment regimen to titrate use of the drugs; determining the need for emergency care; detecting specific allergens or workplace exposures that trigger attacks; facilitating clinical assessment with objective measurements; enhancing compliance of patients with their treatment regimen; and aiding in distinguishing breathlessness due to an acute episode from other causes of breathlessness.

Accurate record keeping is important, and records of peak expiratory flow rate measurements should include the maximum rate, the date and time of measurement, any symptoms, and use of medicants.

Current Limitations in the Field

Currently, personal respiratory care devices that serve the functions of an inhaler and a PEFR are only available as completely separate units. It would be useful to have a combination personal device that serves both of these functions in a single personally portable unit. The field needs such a device to enhance and facilitate patient compliance with their prescribed therapeutic regime, by combining the therapeutic tool (the aerosol medicant inhaler) with the diagnostic tool (the peak flow meter). Too often, patients tend to use their inhaler only when they "feel" the need for it. However, the deterioration of the respiratory condition is detectable using diagnostic means days before a patient can feel the effects of the deterioration. But because the use of the inhaler can give patients the short-term relief they are seeking, they may consider the episode an isolated event which they are able to control, and not realize the magnitude of the deterioration and the seriousness of their respiratory condition. This situation often continues until the respiratory condition is so compromised that the patient suffers a catastrophic episode of respiratory failure requiring emergency medical intervention.

Physicians and other care providers and the patients themselves often do not fully understand the proper techniques involved in administering aerosol medications and how to titrate for proper dose and timing of intervention. Both overuse and under use of aerosol medicants have been frequently noted problems in clinical studies.

The compromise of a patient's airway associated with the allergic reaction in asthma requires very careful monitoring and treatment. Since patients are often unable to completely control their environments or personally predict the onset of an acute allergic reaction, it is useful for them to be equipped to be timely forewarned in order to prevent a full blown asthma attack. Routine self-monitoring and effective self-titrating has been difficult because the necessary equipment was inconvenient to carry and utilize. This inconvenience has exacerbated patient non-compliance with treatment regimens and self-titration, and contributed to increased acute emergency episodes.

Controlled management of a treatment regimen is influenced by many factors. The patient needs to establish personal baseline values for airway responsiveness and then needs to monitor his/her airway responsiveness on a routine basis. Once a deleterious change is noted, the patient needs to initiate the proper medication immediately—and not put off medication because he/she does not "feel " a need for it. The patient then needs to closely monitor their respiratory system's response to effectively self-titrate the treatment regimen or to gather appropriate data to enable their professional care giver to adjust the treatment protocol. After the decline in respiratory condition is arrested, on going evaluation must be performed to titrate the dose to avoid over or under medicating the condition.

To accomplish all of this requires not just patient motivation, but also technical convenience to enhance a patient's compliance with their treatment regimen.

SUMMARY OF THE INVENTION

The present invention as a combination inhaler and peak expiratory flow rate meter (PEFR). In such a combination, the present invention includes an inhaler component and a PEFR component. An object and advantage of this combination includes an aerosol chamber or spacer component. A combination device of the present invention may have elements and features of these components that are shared or modified. For example, the spacer/aerosol chamber in some embodiments may be considered a spacer modified to include elements of the PEFR component. In another embodiment the spacer body/aerosol chamber may be considered a modified element of the inhaler component, such as the mouthpiece adapter/canister housing described above.

A primary object of the present invention is to provide chronic obstructive pulmonary disease (COPD) and similar patients with a means and method to enable them to closely monitor their respiratory system's compliance and response to threapy. Such means and method are necessary to enable patients to effectively self-titrate their treatment regimen or to gather appropriate data to enable their professional care giver to adjust the treatment protocol to avoid over or under medicating their condition.

An object of the present invention is the added benefit of a spacer in combination with a combined inhaler-PEFR.

Another object of the present invention is a one-way mouthpiece valve which in its normal position closes in the content of the aerosol chamber, and prevents a user from exhaling into the aerosol chamber. A further aspect of this object is a one-way vent valve which in its normal position closes in the content of the aerosol chamber, and regulates the user's inhalation rate by controlling the rate of mixing of ambient air with the content of the aerosol chamber during inspiration. One-way valves are within the skill level of the ordinary artisan.

The several elements of the components of the present invention may be integral (i.e., an inseparable part) or may be attachable and removable from the device. With the present teachings at hand, the selection and design of features as integral or attachable/removable is determinable by the ordinary skilled artisan in the art of inhalers and PEFRs.

In the present invention, elements of an inhaler component include a holder for receiving and holding a aerosol canister; a nozzle fitting with a receptacle for receiving the nozzle of an aerosol canister; a nozzle stop as part of the canister activation mechanism; an aerosol discharge path and discharge port integral to the nozzle fitting for dispersing the aerosol; and a chamber (or mouthpiece) for adapting the discharged aerosol for inhalation by a user.

BRIEF DESCRIPTION OF THE DRAWINGS

FIG. 2a: End-on view of first or mouthpiece end of a spacer body showing the separate openings to the aerosol section and to the PEFR section with the exhaled air partitioning chamber behind it and the opening to the PEFR housing behind that.

FIG. 6: View of the longitudinal cross-section through a second end cap that functions as an inhaler holder for a spacer body of FIG. 4a. A second end cap for a spacer body of FIG. 4b would be solid i.e., not have an aperture for inserting a standard inhaler mouthpiece.

FIG. 7: Outside view of body of a spacer body of FIG. 1 showing further details associated with the PEFR housing section of the spacer body.

FIG. 8: A peak expiratory flow rate meter mechanism.

FIGS. 9a & 9b: Views of the pressure sensor's sliding airflow obstruction.

FIGS. 10a & 10b: Views of the pressure sensor's sliding indicator.

FIG. 11: View of the longitudinal cross-section of a fully assembled spacer body of FIG. 4a showing the mouthpiece in position for use with an inhaler.

FIG. 13d: An integral combination inhaler, PEFR and spacer body configured for use as an inhaler.

FIG. 13e: An integral combination inhaler, PEFR and spacer body configured for storage and personal transport.

FIGS. 14a & 14b: An outside friction-fit end cap including a vent valve.

DETAILED DESCRIPTION OF THE INVENTION

Figure 1:
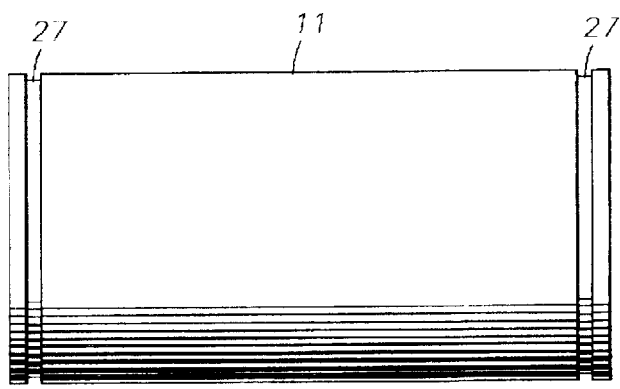
FIG. 1: Outside view of body of a combination spacer and PEFR showing circumferential grooves at each end of the combination spacer body.
Figure 2A:
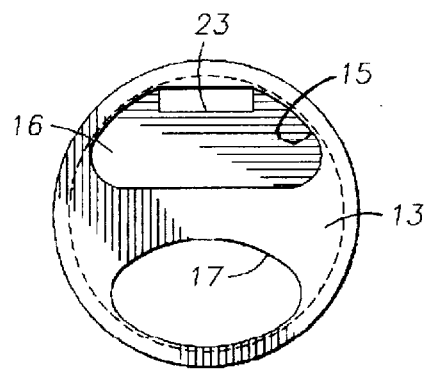
Figure 2B:
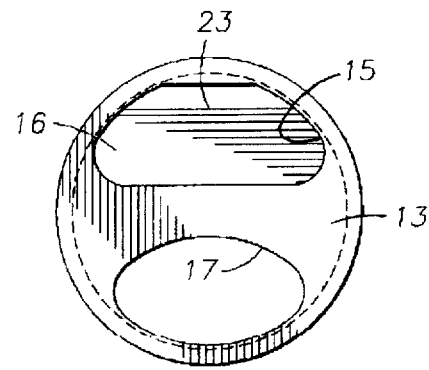
FIG. 2b: View similar to FIG. 2a, but showing a modification of the cross-section of the PEFR housing.
Figure 2C:
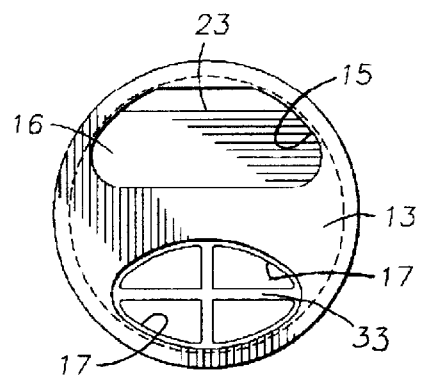
FIG. 2c: View similar to FIG. 2a, but showing a modification of the aerosol aperture to include a one-way valve section.
Figure 2D:
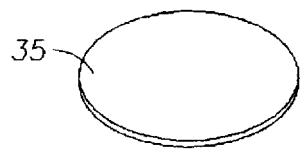
FIG. 2d: View of a flexible diaphragm for use in a one-way valve of FIG. 2c.
Figure 3:
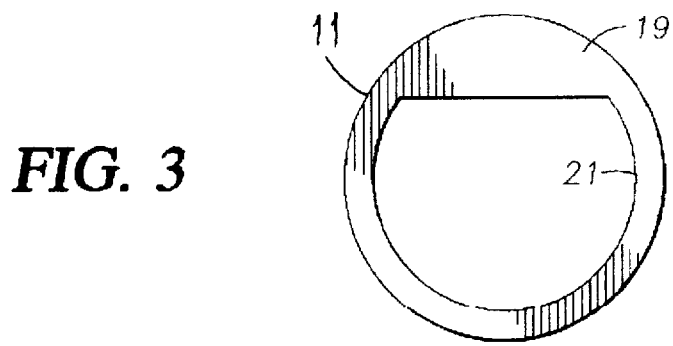
FIG. 3: End-on view of a second end of a spacer body showing an opening to the aerosol section.

The FIGS. 1 to 11 show as a present preferred embodiment, the spacer component as the body of the device is integral with the peak expiration flow rate meter component. In this specific embodiment, the invention comprises a hollow spacer body 11 cylindrical in shape, and having a first mouthpiece end 13 and a second aerosol inlet end 19. The interior of the spacer body 11 is divided into a flow sensor housing 23 and an aerosol chamber 25. The exterior of the spacer body 11 has a circumferential groove 27 located proximal to each of the ends.

The mouthpiece end 13 has two openings that separately communicate with an interior section of the spacer body 11. One opening is a partitioning chamber/mouthpiece interface aperture 15, which communicates with partitioning chamber 16. The partitioning chamber 16 is then in communication with the flow sensor housing 23. The other opening is an aerosol chamber/mouthpiece interface aperture 17, which communicates with the aerosol chamber 25. The aerosol inlet end 19 has a single opening, the aerosol inlet aperture 21, which communicates with the aerosol chamber 25.

In a preferred embodiment the invention also includes a one-way valve. In this specific embodiment, aerosol chamber/mouthpiece interface aperture 17 includes a one-way valve comprising the combination of a flexible diaphragm 35, a one-way valve housing 33.

A mouthpiece 37 is provided which is detachably connectable to the spacer body 11 by the engagement of a circumferential groove 27 on the spacer body 11 and the groove engagement lip 41 of the mouthpiece 37. The engaged combination of the mouthpiece 37 and the spacer body 11 are rotatable relative to each other and permits positioning of the mouthpiece passage 47 to be in communication with either one of the flow sensor housing 23, or the aerosol chamber 25 of the spacer body 11, while sealing off the other section. A second-end cap 39 (FIG. 6) is provided which is detachably connectable to the spacer body 11 by the engagement of a circumferential groove 27 on the spacer body 11 and the groove engagement lip 41 of the second end cap 39. In this embodiment, the second end cap 39 has an aerosol dispenser aperture 43 which allows the mouthpiece of an inhaler device to be inserted through second-end cap 39 and into communication with the aerosol chamber 25 of the spacer body 11.

Figure 4A:
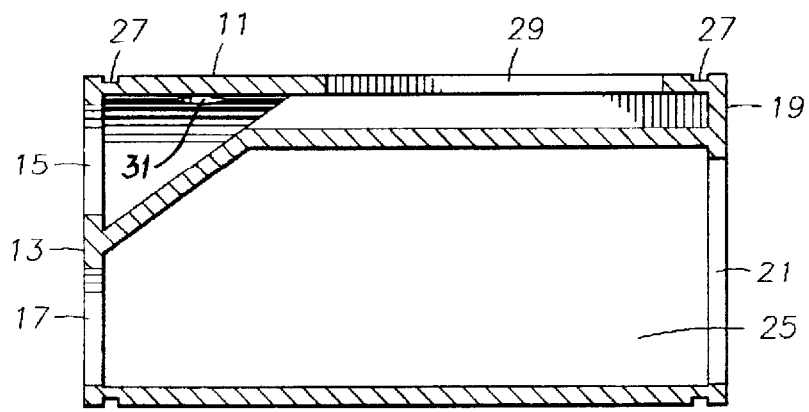
FIG. 4a: View of the longitudinal cross-section of a spacer body that is a combination spacer/PEFR.
Figure 4B:
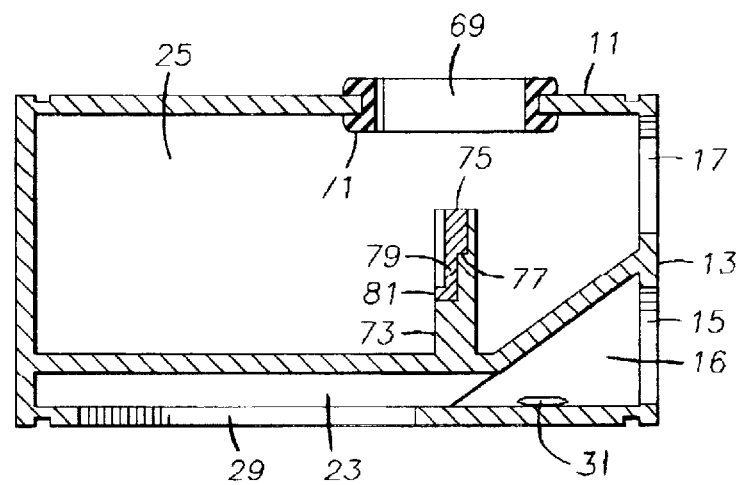
FIG. 4b: View of the longitudinal cross-section of a spacer body that is a combination spacer/PEFR/holder. This embodiment differs from FIG. 4a in that the holder and its associated elements are integral to the spacer body, and the FIG. 5: View of the longitudinal cross-section through a mouthpiece for a spacer body.

In an alternative preferred embodiment, a second-end cap 38 is solid, i.e., it does not have an aerosol dispenser aperture 43. In this case, as communication of an aerosol dispenser with the aerosol chamber 25 of spacer body 11 is accomplished by other means, such as shown in FIG. 4b. This embodiment comprises, means for accepting a standard metered dose inhaler (MDI) canister 67 that are an integral part of the aerosol chamber 25 of the spacer body 11. As shown in FIG. 4b, the present invention includes an inhaler component, a spacer component and a PEFR component. More specifically, aerosol chamber 25 of spacer body 11 includes the elements of a metered dose inhaler cannister housing as integral parts of aerosol chamber 25. In the instant embodiment, the inhaler housing features are placed proximal to mouthpiece end 13 of aerosol chamber 25. The inhaler housing comprises a canister opening 69 and cannister holder 71, which in this embodiment is grommet-like, through the opening of which a standard aerosol canister 67 is inserted and held in place; and a canister nozzle fitting 73 having a nozzle receptor 75 for accepting a canister nozzle, a nozzle seat 77 against which the nozzle of the canister is pressed to actuate the canister, an aerosol discharge path 79 and discharger port 81. In this embodiment, the discharge port 81 directs the dispensed aerosol cloud longitudinally down the length of the aerosol chamber 25, away from mouthpiece end 13, and toward the second-end 19.

FIGS. 8, 9 and 10 show details of a piston-type flow sensor. Piston type flow sensor mechanisms are known in the art. (See Bellofatto et al. U.S. Pat. No. 5,224,487 and Alvino U.S. Pat. No. 4,944,306). The flow sensor assembly 49 is positioned in the flow sensor housing 23 of the spacer body 11 by attaching the rod mounts 61 to the flow sensor housing 23 and allowing sliding indicator 57 to protrude into the flow sensor indicator aperture 29, with the sliding airflow obstruction (piston) 53 at the lower end of the scale marks 45. In this embodiment, the lower end of the scale marks 45 is toward the mouthpiece interface end 13 of the spacer body 11.

In this combination of elements, the sliding indicator 57 will be pushed down rod 51 against the combined resistance of variable resistor 55 and fixed resistor 59 a distance representative of the peak flow rate of the exhaled gas.

The components of the flow sensor assembly 49 and the features of the flow sensor housing 23, are selectable by one skilled in the art to accomplish a desired specific application of the invention, i.e., for use by children versus use by adults.

Operation as a peak expiratory flow rate meter (PEFR)

In operation as a PEFR, mouthpiece 37 is rotatably positioned so that the mouthpiece passage 47 is in communication with the flow sensor housing 23 of the spacer body 11. In a preferred embodiment, upon rotating into the proper position for use as a peak flow rate meter, the mouth piece would lock into such position to assure a proper relationship between the mouthpiece passage 47 and aperture 15 in mouthpiece end 13.

Sliding indicator 57 is manually positioned to be adjacent the sliding airflow piston 53 at the low reading end of the scale marks 45. A user of the invention "explosively" exhales (with a maximal effort) into the mouthpiece 37. The exhaled gas passes through the mouthpiece passage 47, through partitioning chamber/mouthpiece interface aperture 15 in mouthpiece end 13 and enters partitioning chamber 16. In partitioning chamber 16, part of the exhaled air is directed into the flow sensor housing 23, and excess exhaled air flow is vented from the device through a flow bypass aperture 31.

Upon entering the flow sensor housing 23, the exhaled gas exerts pressure on the sliding airflow piston (obstruction) 53 causing it to slide down rod 51, against the increasing resistance of variable resistor 55 and the resistance of fixed resistor 59, while pushing sliding indicator 57 in front of it. The distance that indicator 57 is pushed along the scale marks 45, provides an indication of the peak flow rate of the exhaled gas. Any of this exhaled air which is or becomes insufficient to effect the flow sensor assembly 49 is vented from the device via the flow sensor housing indicator aperture 29.

The peak expiratory flow rate of the user's exhalation then is determined by reading from the scale marks 45 the flow rate indicated by the sliding indicator 57. Units for scale marks 45 are selected by the skilled artisan and the value assigned to the marks are established by the design of the device and empirical analysis.

Components and features that are selectable by the skilled artisan in this embodiment include:

cross sectional area of the flow sensor housing 23, particularly with regard to the cross sectional area of the sliding gas-flow obstruction 53.

specific range of resistance per length of variable resistor 55. The variable resistor in this embodiment is a calibrated spring having a precise increasing stretch resistance (Hook's constant) to increases in its length from a shorter length to a longer length. Lengthening of the spring variable resistor 55 is proportional to the maximum pressure created by the user's exhalation effort.

resistance of fixed resistor 59.

cross sectional area of excess flow bypass apertures 31.

cross sectional area of flow sensor indicator aperture 29.

Generally, for users with expiratory flow rates that tend to be relatively low, such as young children or those with some form of chronic respiratory deficiency, the relevant features and components can be designed or selected to accommodate the application of the invention to the class of user's needs. By pass apertures 3 1 can be reduced or eliminated, resistors can be selected to reduce the overall resistance of the assembly 49, cross sectional areas can be appropriately adjusted.

Operation as an inhaler

If the spacer body 11 is used to store a canister 67 or a canister-holder combination, second-end cap 39 (or 38) is removed, the canister 67 or canister-holder combination is removed from the aerosol chamber and the second-end cap 39 (or 38) is replaced.

The mouthpiece 37 is rotated so that mouthpiece passage 47 is in communication with the aerosol chamber 25 of spacer body 11. In a preferred embodiment, upon rotating into the proper position for use as an inhaler, the mouth piece would lock into such position to assure a proper relationship between the mouthpiece passage 47 and opening 17 in mouthpiece interface 13. Design and implementation of an appropriate locking means is within the capacity of one of ordinary skill in the art.

Figure 12:
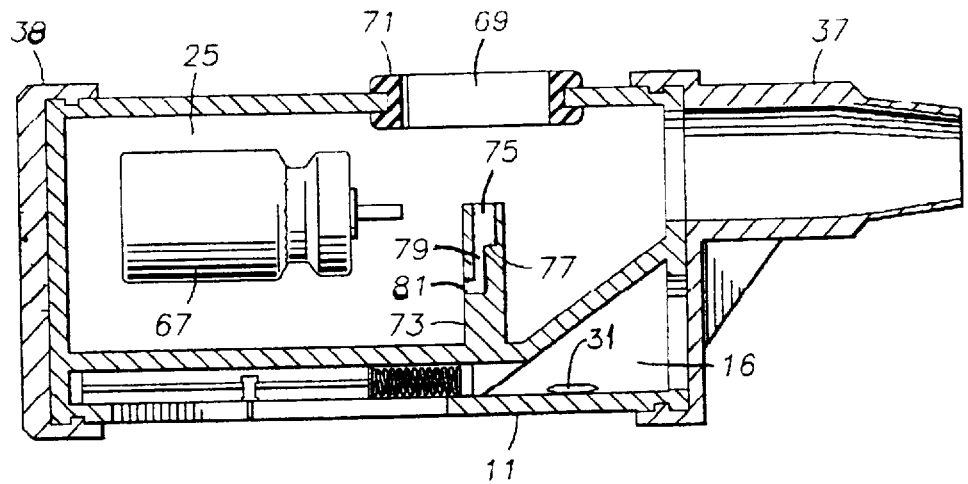
FIG. 12: View of the longitudinal cross-section of a fully assembled spacer body of FIG. 4b showing the mouthpiece in position for use with an inhaler.

A standard inhaler canister holder combination is inserted into the aerosol dispenser holder aperture 43 of second-end cap 39 (see FIG. 6), or alternatively, a canister 67 is inserted nozzle first through the center of canister holder 71 with its nozzle seated in nozzle receptor 75 (see FIG. 12). The canister is actuated to dispense its dose into aerosol chamber 25. Using mouthpiece 37, the user inhales by mouth, the aerosol contained in the aerosol section 25 of spacer body 11.

The presence of a one-way valve (FIGS. 2c & 2d) permits aerosol chamber 25 to be filled with an aerosol cloud before the user actually inhales through the device, or coincident with the user's inhalation. This feature has the advantage of not requiring the user to coordinate the act of inhalation with the act of dispensing the medicant from the dispenser/canister, by allowing the aerosol cloud to be dispensed into the aerosol chamber 25 and trapped there momentarily by the one-way valve, before the user inhales through the device. This feature additionally allows a second party to charge the device with aerosol and then give it to the user. An advantage of this feature is that it uncouples the act of dispensing the aerosol from the act of inhaling the aerosol cloud. This provides a method of overcoming dexterity and coordination problems commonly experienced by pediatric and geriatric users. This feature allows a second party to charge the device and then coach the user through the inspiratory act. Further, this feature prevents the user from accidentally exhaling through the device and inadvertently not receiving a full dose of medication.

The device may then be wiped or rinsed to remove residue medicant. The second-end cap 39 (or 38) may be removed and the aerosol canister 67 stored inside the aerosol chamber 25 until the device's next use, and the second end-cap 39 (or 38) replaced.

Figure 13B:
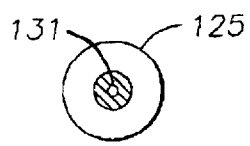
FIGS. 13b & 13c: Views of the ends of a nozzle fitting showing the nozzle fitting key and the canister nozzle receptor aperture.
Figure 13C:
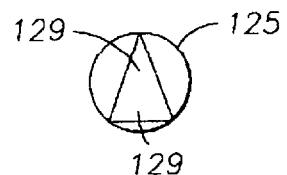
Figure 13A:
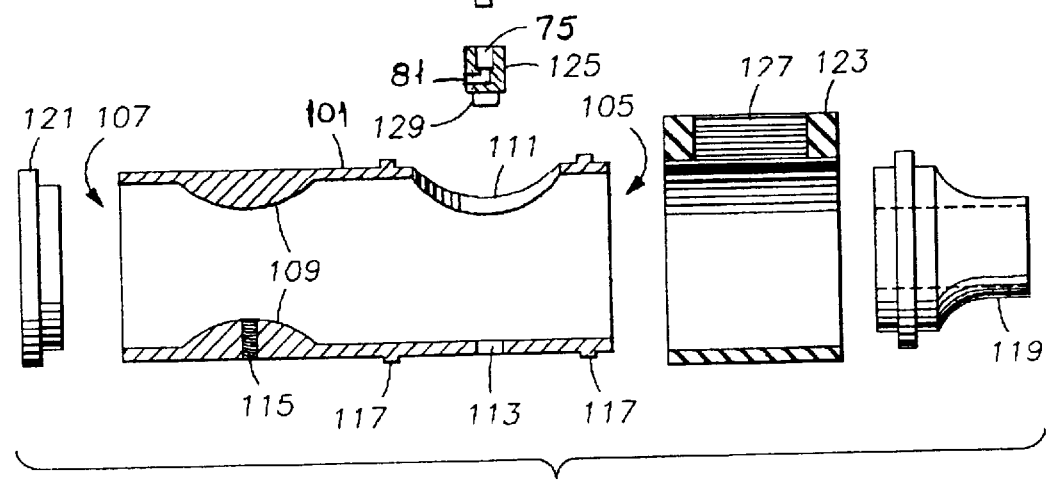
FIG. 13a: An integral combination inhaler, PEFR and spacer body. Longitudinal cross-section of a spacer body, nozzle fitting and canister holder sleeve, and full view of other components.

Another preferred embodiment of the present invention is demonstrated in FIGS. 13, and comprises a tubular spacer body 101, forming aerosol chamber 103, having a first mouthpiece end 105 and a second pressure sensor end 107. The lumen of spacer body 101 includes a venturi feature 109 encircling the inner surface of aerosol chamber 103 proximal to pressure sensor end 107. Additionally, a wall of spacer body 101 has a canister aperture 111, a nozzle fitting key aperture 113, a venturi tube 115, and sleeve guides 117. This embodiment further comprises a mouthpiece 119, an end cap 121, a canister holder grommet sleeve 123, and a canister nozzle fitting 125.

When air from the user's lungs is flowing through the lumen of the spacer body 101, the venturi feature 109 created a pressure difference between the gas flow in the vicinity of the venturi 109 relative to the pressure in the gas flow elsewhere in the lumen. This difference in pressure is explained by Bernoulli's Principle: the observation that as the velocity of a liquid or gas increases, the pressure within the liquid or gas decreases. Bernoulli's Principle states that the total energy in a constant flow system at any instant is constant everywhere along the flow path. Therefore, an increase in the flow's velocity at a point in the flow path is matched by a decrease in pressure at that point. The pressure difference caused by the venturi effect relative to ambient air pressure is transmitted via venturi tube 115 to the outside surface of the spacer body 101. At the outside surface of the spacer body 101, a pressure sensor transducer is interfaced with the venturi tube 115, and the pressure of expired air flowing inside the spacer body 101 due to the venturi effect can be measured. The greater the venturi effect (decrease in pressure) the higher the velocity of the gas flowing in the lumen of the spacer body 101. Depending on the capabilities of the particular pressure sensor transducer being used, a series of instantaneous pressure measurements may be made and the peak expiratory flow rate determined or a single determination of the peak expiratory flow rate may be made.

Bernoulli's Principle and its use in venturi flow meters is old in the art and the ordinary skilled artisan, with the present teachings at hand, would be able to adapt a venturi flow meter to serve as a pressure sensor mechanism for use with the present invention. As the fields of solid state electronics and sensor and storage device miniaturization continues to progress, the range of useful pressure sensor transducers available to the skilled artisan for application in the present invention also continues to grow.

When not in use, the device stores an aerosol dispenser canister 67 in the lumen of the spacer body 101. Nozzle fitting 125 may be stored loose or in place on the nozzle of the stored canister 67. See FIG. 13e. End cap 121 is inserted in the mouthpiece end 105 of the spacer body to retain the canister in place. In this embodiment, end cap 121 is held in place by a friction fit. Mouthpiece 119 is inserted into the second pressure sensor end 107 of spacer body 101 as shown in FIG. 13d, with the mouthpiece itself nested inside the lumen of the spacer body 101, and similarly held in place by friction. The canister holder grommet sleeve 123 is stored in its place girting spacer body 101.

To configure the device for use as a PEFR (see FIG. 13a), the end cap 121, mouthpiece 119 and canister 67 are removed from the device. Optionally, the device may be designed for the mouthpiece 119 to be used in place. The canister holder sleeve 123 is rotated around the outside of the spacer body 101 so as to occlude canister aperture 111 and nozzle key aperture 113. The venturi tube 115 opening at the outside surface of the spacer body 101 is brought into communication with a pressure sensor transducer. In this configuration, a user explosively exhales into mouthpiece 119 of the device. The exhaled air flows through the lumen of the spacer body 101 across the venturi feature 109. A pressure decrease is caused at the venturi 109 proportional to the flow rate of the passing gas. The pressure at the venturi 109 is transmitted via the venturi tube 115 to the pressure transducer and measured. A peak expiratory flow rate is determined from the from the greatest instantaneous decrease in venturi pressure measure during the exhalation.

To configure the device for use as an inhaler (see FIG. 13d), the end cap 121 and mouthpiece 119 are removed from the device, and canister 67 is retrieved from its storage place inside the device. If the nozzle fitting 125 is not in place, it is set in place over the nozzle of the canister 67. The mouthpiece 119 is inserted into position on the first mouthpiece end 105 of the spacer body 101. The end cap 121 is inserted to cover the second pressure sensor end 107 of the spacer body 101. The canister holder sleeve 123 is rotated about the girth of the spacer body 101 to align cannister aperture 127 in sleeve 123 with the canister opening 111 in the spacer body 101. The nozzle of canister 67 is inserted into nozzle receptacle 131 and the combination, with nozzle fitting in place, is inserted into the device through eye 127 of grommet sleeve 123. Upon insertion of the canister/nozzle fitting combination, the nozzle key 129 on the nozzle fitting 125 is aligned and inserted into key aperture 113 on the inside of the spacer body 101. Engagement of the nozzle key 129 and key aperture 113 ensures the discharge port 81 of the nozzle fitting 125 is properly positioned in the aerosol chamber 103.

In this configuration, a user places mouthpiece 119 of the device into his/her mouth with the canister 67 vertical and on the top-most side of the spacer body 101. The user covers or plugs the outside opening of the venturi tube 115 (with a thumb or finger or otherwise). The user then actuates canister 67 and quickly thereafter inspires the content of the aerosol chamber 103 by mouth.

It is preferred that the spacer body 101 or mouthpiece 119 include a one-way valve to accomplish the objects and advantages in this embodiment as noted herein for other embodiments. Design and inclusion of a one-way valve in this embodiment is accomplishable by one of ordinary skill in this art, using any of a number of means available to the skilled artisan, including the means described above.

Any embodiment of the present invention may include a means for admitting additional air into the aerosol chamber during the act of inspiration by the user. Such means may be accomplished in any of a number of manners by the ordinary skilled artisan. An example of such means is shown in FIGS. 14a & 14b, where an end cap 141 has one or more vent apertures 135 that are normally covered by a diaphragm 137 until a user's inhalation causes a reduction in pressure in the aerosol chamber of the device, which allows air to be drawn through the vent apertures 135, past the diaphragm 137 and into the aerosol chamber of the device. The end cap 141 has a button 139 or similar feature for attaching the diaphragm 137 by means of button aperture 143 to the inner surface of end cap 141. FIGS. 14a & 14b shows details of such a venting means on an outside friction fit end cap 141.

This combination of features forms a flapper valve that is normally closed and prevents aerosol medicant from being vented from a device of the present invention after its canister has been activated and the aerosol chamber is charged with medicant. Upon a user's inhalation, a negative pressure is developed in the aerosol chamber and ambient air rushes past the flapper valve at a rate modulated by the total cross-sectional area of the vent apertures and carries the aerosol from the chamber. The object of the vent apertures is to prevent a user from inhaling too quickly, and the design of the cross-sectional area of the apertures is selectable by the skilled artisan to suit the needs of an individual or a class of user. The apertures may be designed to be either fixed or variable, as the skilled artisan chooses.

Figure 15A:
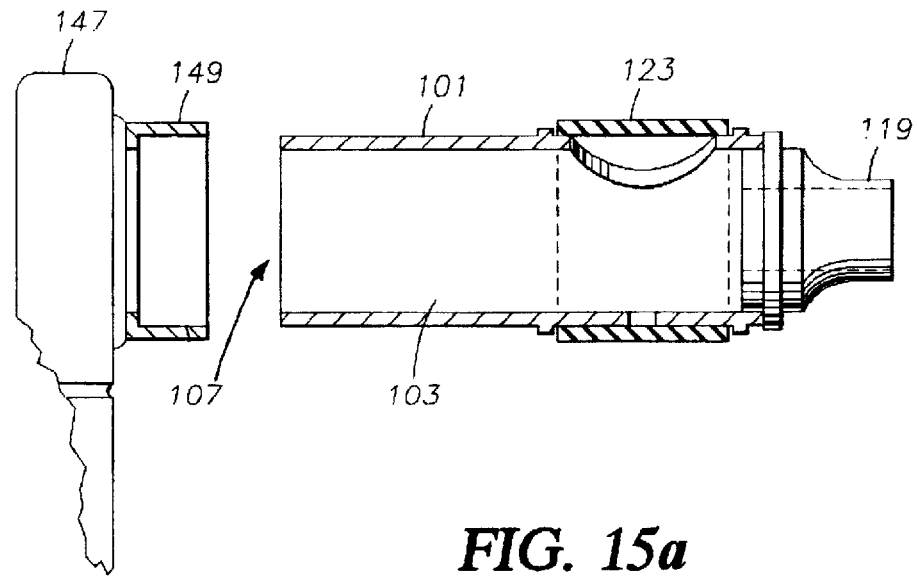
FIGS. 15a & 15b: A device of the present invention configured for use with a personal spirometer.
Figure 15B:
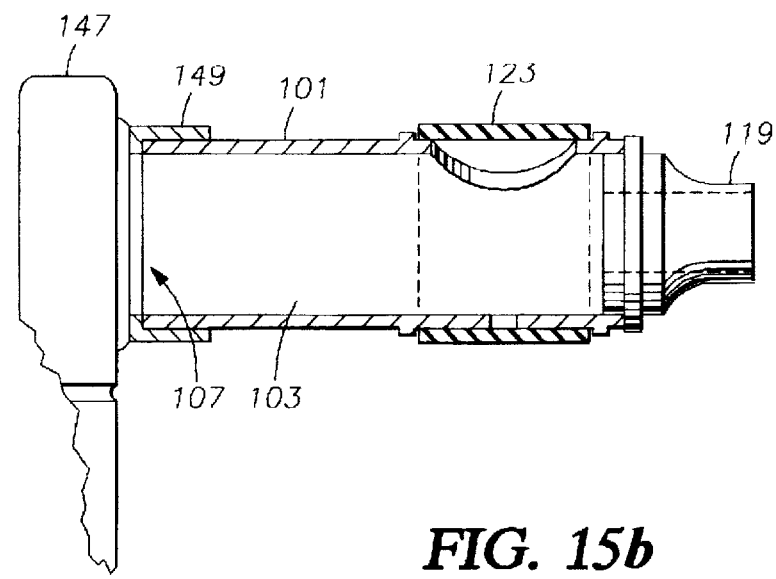

An additional preferred embodiment of the present invention is shown in FIGS. 15a and 15b, and comprises a hollow spacer body 101 and a second pressure sensor end 107 having featureless lumen walls (i.e., not having a venturi feature nor a venturi tube). The remainder of spacer body 101 is analogous to that shown in FIG. 13. The pressure sensor transducer 147 in this embodiment is a magnetically coupled spirometer having an inlet tube 149 that is connectable to the second pressure sensor end 107 of spacer body 101.

To configure this embodiment for use as a PEFR, the end cap 121, mouthpiece 119 and canister 67 are removed from the device. (Optionally, the device may be designed for the mouthpiece 119 to be used in place). The canister holder sleeve 123 is rotated around the outside of the spacer body 101 so as to occlude canister aperture 111 and the nozzle key aperture 113.

The transducer inlet tube 149 is connected to the pressure sensor end 107 of spacer body 101. In this configuration, a user explosively exhales into the mouthpiece end 105 of the device. The exhaled air flows through aerosol chamber 103 of spacer body 101 and into transducer inlet tube 149 of the spirometer. The user's peak expiratory flow rate is registered on the spirometer. A magnetically coupled spirometer suitable for use in this embodiment includes the MICRO SPIROMETER™ and the MICRO PLUS SPIROMETER™ (Micro Medical LTD., Kent, England).

The device of this embodiment is configured for use as an inhaler in a manner analogous to that described above for the device of FIGS. 13. Use of this embodiment as an inhaler is also analogous, except there is no venturi tube opening to be covered or plugged.

While the above description contains many specifics, these should not be construed as limitations on the scope of the invention, but rather as exemplifications of one or another preferred embodiment thereof Many other variation are possible, which would be obvious to one skilled in the art. Accordingly, the scope of the invention should be determined by the scope of the appended claims and their equivalents, and not just by the embodiments.

What is claimed is:

1. A personal portable respiratory care device comprising:

a spacer component having a hollow substantially cylindrical shaped body, and an interior of the body being divided into a flow sensor housing for housing a peak expiratory flow rate meter, and an aerosol chamber into which a dose of an inhaler's content is dispensed before or during an act of inhalation by a user and which retains a portion of the dispensed dose that would otherwise rain-out in the user's mouth and throat, and the spacer body including a first mouthpiece end having two openings that separately communicate with the flow sensor housing and the aerosol chamber, and a second aerosol inlet end sealed with a second end cap having an aerosol inlet aperture, which communicates the aerosol chamber with an inhaler component;

an inhaler component having a canister containing a pharmaceutical formulation and a metering valve that controls the dose of formulation dispersed during a single actuation of the valve, a holder for housing the canister, a nozzle fitting for receiving and directing the dose expelled from the canister on activation into the aerosol chamber and adapting the dose to an aerosol cloud for inhalation by the user;

a peak expiratory flow rate meter component housed within the flow sensor housing of the spacer body for measuring the maximum rate at which air is expelled out of the user's lungs during the course of an explosive exhalation, and the housing having a calibrated scale, a mouthpiece port an indicator, and an expiratory port for exhausting expired air; and a mouthpiece at the mouthpiece end of the spacer body having a passage therethrough, and adapted for positioning the passage to be in selected communication with either one of the flow sensor housing or the aerosol chamber of the spacer body while sealing the other off.

2. The device of claim 1, wherein the spacer component comprises: an aerosol chamber having a one-way valve located proximate the mouthpiece end of the aerosol chamber, for preventing the user from exhaling through the aerosol chamber of the device and inadvertently not receiving a full dose.

3. The device of claim 2 wherein: the aerosol chamber of the spacer body has a second one-way valve located proximate a second end, which modulates the rate of air flow into the device during a patient's inspiration of the content of the device.

4. The device of claim 1 wherein the inhaler component comprises:

a holder for receiving and holding an aerosol canister, which canister is for dispensing an aerosol entrapped product;

a fitting for receiving a nozzle of the aerosol canister;

an aerosol discharge path; and a discharge port for directing the aerosol.

5. The device of claim 1 wherein the peak expiratory flow rate meter component comprises:

a peak expiratory flow rate meter mechanism;

a scale;

a housing for the peak expiratory flow rate meter mechanism; and a means for combining the housing and the inhaler component.

6. The device of claim 5 wherein the peak expiratory flow rate meter component comprises:
- a peak expiratory flow rate meter mechanism having a means adapted for retaining a measurement of peak air flow through said meter component;
- a scale for displaying a measurement of air flow through said meter component;
- a housing for the peak expiratory flow rate meter mechanism, the housing having an air flow inlet and an air flow outlet; and
- a means for combining the housing and the inhaler component.

7. The device of claim 6 wherein the peak expiratory flow rate meter mechanism comprises a spring-biased piston and an indicator, slidably mounted in series on a rod and slidable along the rod in response to air flow through the meter component, the indicator communicating with the scale to display the measurement of air flow rate through the meter component.

8. The device of claim 1 wherein the spacer component is integral with the inhaler component, and the peak expiratory flow meter component is removably attachable from the integrated spacer and inhaler components.

9. The device of claim 1 wherein the spacer component is integral with the peak expiratory flow rate meter component, and the inhaler component is removably attachable from the integrated spacer and peak expiratory flow rate meter components.

10. The device of claim 1 wherein the spacer component, the peak expiratory flow rate meter component and the inhaler component are an integral unit.

11. A method of facilitating an asthma patient's compliance with a therapeutic regimen, which regimen requires the use of both an inhaler and a peak expiratory flow rate meter, comprising the steps of:

providing said patient with a combination inhaler and peak expiratory flow rate meter device of claim 1, thereby making both of said inhaler and peak expiratory flow rate meter simultaneously available to said patient to facilitate said patient's compliance with said therapeutic regimen; and instructing said patient in the use of the device of claim 1.

12. The device of claim 1, wherein the spacer component comprises:
- a hollow substantially cylindrical shaped body, and the interior of the body being divided into a flow sensor housing for housing a peak expiratory flow rate meter, and an aerosol chamber into which a dose of an inhaler's content is dispensed before or during an act of inhalation by a user, and the spacer body including a first mouthpiece end having two openings that separately communicate with the flow sensor housing and the aerosol chamber, and a second end sealed with a second-end cap; and
- a means for accepting a standard metered dose inhaler canister integral to the aerosol chamber of the spacer body, the accepting means including a canister opening in the spacer body communicating with the aerosol chamber and located proximate the mouthpiece end of the aerosol chamber, a cannister holder received in the canister opening through which a standard aerosol canister is insertable and held in place, and a canister nozzle fitting having a nozzle receptor for accepting a canister nozzle, a nozzle seat against which the nozzle of the canister is pressed to actuate the canister, an aerosol discharge path and discharger port, which directs a dispensed aerosol cloud longitudinally down the length of the aerosol chamber, away from mouthpiece end, and toward the second-end of the spacer body.

* * * * *